United States Patent [19]

Roth et al.

[11] Patent Number: 5,079,129
[45] Date of Patent: Jan. 7, 1992

[54] NEGATIVE PHOTORESIST BASED ON POLYPHENOLS AND EPOXY COMPOUNDS OR VINYL ETHERS

[75] Inventors: Martin Roth, Giffers; Kurt Meier, Allschwil, both of Switzerland

[73] Assignee: Ciba-Geigy Corporation, Ardsley, N.Y.

[21] Appl. No.: 445,134

[22] Filed: Nov. 30, 1989

Related U.S. Application Data

[63] Continuation of Ser. No. 79,624, Jul. 30, 1987, abandoned.

[30] Foreign Application Priority Data

Aug. 6, 1986 [CH] Switzerland ............. 3157/86

[51] Int. Cl.$^5$ .......... G03F 7/029; G03F 7/033; G03F 7/037; G03F 7/004
[52] U.S. Cl. ............. 430/280; 430/288; 430/281; 430/176; 430/905; 522/31; 522/66; 522/121; 522/120; 522/129; 522/141; 522/142; 522/146
[58] Field of Search .......... 430/280, 288, 281, 176, 430/905; 522/31, 66, 121, 120, 129, 141, 142, 146

[56] References Cited

U.S. PATENT DOCUMENTS

| | | | |
|---|---|---|---|
| 3,030,332 | 4/1962 | Lombardi et al. | 260/43 |
| 3,497,353 | 2/1970 | Steppan et al. | 96/35.1 |
| 3,558,535 | 1/1971 | Rushton et al. | |
| 3,708,296 | 1/1973 | Schlesinger | |
| 3,869,292 | 3/1975 | Peters | |
| 3,936,557 | 2/1976 | Watt | 428/211 |
| 4,090,936 | 5/1978 | Barton | 96/115 P |
| 4,148,654 | 4/1979 | Oddi | 96/35.1 |
| 4,193,799 | 3/1980 | Crivello | |
| 4,273,889 | 6/1981 | Yamazaki et al. | 525/109 |
| 4,289,699 | 11/1981 | Oba et al. | |
| 4,339,567 | 7/1982 | Green et al. | |
| 4,383,025 | 5/1983 | Green et al. | |
| 4,398,014 | 8/1983 | Green et al. | |
| 4,407,759 | 10/1983 | Crivello | 260/440 |
| 4,442,197 | 4/1984 | Crivello et al. | 430/280 |
| 4,537,854 | 8/1985 | Crivello | |
| 4,549,008 | 10/1985 | Renner et al. | |
| 4,579,916 | 4/1986 | Schmid et al. | 525/502 |
| 4,593,051 | 6/1986 | Koleske | 522/146 |
| 4,624,912 | 11/1986 | Zweifel et al. | |
| 4,632,971 | 12/1986 | Cavitt | 528/88 |
| 4,678,737 | 7/1987 | Schneller et al. | 430/270 |

FOREIGN PATENT DOCUMENTS

| | | |
|---|---|---|
| 0118748 | 9/1984 | European Pat. Off. |
| 124292 | 11/1984 | European Pat. Off. |
| 0174510 | 3/1986 | European Pat. Off. |
| 0222187 | 5/1987 | European Pat. Off. |
| 206518 | 1/1984 | Fed. Rep. of Germany |
| 60-71657 | 4/1985 | Japan |
| 2009435 | 6/1979 | United Kingdom |
| 1549653 | 8/1979 | United Kingdom |
| 1565671 | 4/1980 | United Kingdom |

OTHER PUBLICATIONS

K. Meier and H. Zweifel, "Photoinitiated Cationic Polymerization of Epoxides with Iron-Arene Complexes", *Journal of Radiation Curing*, Oct., 1986, pp. 526–532.
C.A., 104, 43202a (1986).
C.A., 105, 62301w (1986).
C.A., 100, 105179b (1984).
C.A., 102, 176532p (1985).
Derwent Abst. 85-132647/22.
C.A. 103:55104n (1985), Chemical Abstracts of Japanese Laid Open at Patent Application 60-51,770 (Mar. 23, 1985).
Patent Abst. of Japan, vol. 6, No. 237 (1982).
C.A. 70:68780 (1969).
C.A. 103:132418x (1985).
Patent Abst. of Japan, vol. 9, No. 299.

*Primary Examiner*—Cynthia Hamilton
*Attorney, Agent, or Firm*—Harry Falber

[57] ABSTRACT

The present invention relates to a negative photoresist consisting essentially of
a) at least one solid film-forming polyphenol,
b) at least one compound which contains at least two epoxide groups or at least two vinyl ether groups or at least one epoxide and vinyl ether group in the molecule,
c) at least one cationic photoinitiator for component b) and
d) if appropriate customary additives.

The resist can be developed under aqueous-alkaline conditions.

13 Claims, No Drawings

NEGATIVE PHOTORESIST BASED ON POLYPHENOLS AND EPOXY COMPOUNDS OR VINYL ETHERS

This application is a continuation of application Ser. No. 079,624, filed 07/30/87 now abandoned.

The present invention relates to a composition containing essentially polyphenols and epoxy compounds or vinyl ethers, a process for the production of relief structures and the use of the said compositions as a negative resist which can be developed under aqueous conditions.

Epoxy-based negative resists are known. European Patent No. A-153,904 describes a process for the production of protective coatings and of relief structures, such a radiation-sensitive film being used. The system is developed with organic solvents.

British Patent No. A-2,009,435 describes negative resists which can be developed under purely aqueous conditions, a water-soluble or swellable binder, inter alia polyvinyl alcohol, and an acrylic monomer being used as polymerizable components Acrylate-based systems are in general inferior to epoxy systems in respect of mechanical and electrical properties, temperature stability and adhesion to the substrate. Moreover, in contrast to systems which can be developed under alkaline-aqueous or acid-aqueous conditions, systems which can be developed under purely aqueous conditions are relatively sensitive to moisture and have a limited storage stability.

European Patent No. A-124,292 describes an aqueous dispersion of an epoxy resin and an onium photoinitiator The composition is used for the production of protective coatings and of relief images and can be developed under aqueous conditions. Wetting agents or protective colloids, for example polyvinyl alcohol, are preferably added to the dispersions. However, not every epoxy resin is suitable; thus, in some cases, a reactive diluent must be added in order to guarantee dispersibility.

It has now been found that epoxy resin- or vinyl ether-based films which can be developed under aqueous-alkaline conditions can be produced by using a polyphenol or a mixture of polyphenols as the binder.

The present invention relates to a negative photoresist consisting essentially of a) at least one solid film-forming polyphenol,
b) at least one compound which contains at least two epoxide groups or at least two vinyl ether groups or at least one epoxide and one vinyl ether group in the molecule,
c) at least one cationic photoinitiator for component b) and
d) if appropriate customary additives.

The binder a) is a solid film-forming polyphenol, that is to say a polymer which has a certain content of phenolic hydroxyl groups. This should be at least high enough to guarantee development or at least swelling in an aqueous-alkaline developer solution.

Suitable film-forming binders a) which are soluble in alkaline-aqueous systems can in general be divided into the following groups:

i) novolaks of at least one phenol and at least one aldehyde,
ii) homo- and copolymers of alkenylphenols and, in particular,
iii) homo- and copolymers of N-hydroxyphenylmaleimides.

Groups ii) and iii) are preferred here.

Preferred novolaks i) are compounds which are derived from a $C_1$–$C_6$-aldehyde, for example formaldehyde and acetaldehyde, and from a dinuclear, but preferably a mono-nuclear, substituted or unsubstituted phenol. Examples of preferred phenols are phenol itself or phenols which are substituted by one or two $C_1$–$C_9$-alkyl groups, such as, for example, o-, m- or p-cresol, xylenol, p-tert.butylphenol and o-, m- or p-nonylphenol, or phenols which are substituted by one or two halogen atoms, preferably chlorine or bromine, for example p-chlorophenol, phenols which are substituted by a phenyl nucleus, for example p-phenylphenol, or phenols with more than one phenolic group, for example resorcinol, bis-(4-hydroxyphenyl)-methane or 2,2-bis-(4-hydroxyphenyl)-propane.

Preferred homo- or copolymers of alkenylphenols ii) are, in particular, the compounds of the formula I

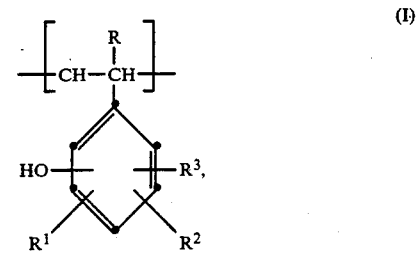

in which R is hydrogen or methyl and $R^1$, $R^2$ and $R^3$ independently of one another are $C_1$–$C_4$-alkyl, $C_1$–$C_4$-alkoxy, halogen, in particular chlorine or bormine, or methylol. The pheonolic hyroxyl group is arranged in the o-, m- or p-position relative to the alkenyl group, but preferably in the p-position.

Examples of possible comonomers are vinyl monomers which are free from carboxyl groups. Examples of such monomers are styrene, acrylates and methacrylates, in particular methyl (meth)acrylate or 2-hydroxyethyl (meth)acrylate, acrylamide, vinyl acetate and N-substituted maleimide.

The comonomer content of the binders of type ii) is preferably 0–50 mol %, based on the total polymer.

Polymers of type ii) are known and are described, for example, in German OffenLegungsschrift 2,322,230 and in European Patent A-153,682. Some such polymers are also commercially available.

Preferred binders of type iii) are homopolymers of N-hydroxyphenylmaleimides. These are preferably homopolymers with the structural unit of the formula II

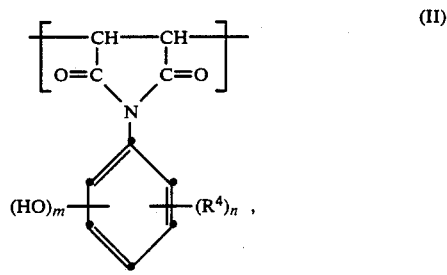

in which $R^4$ is $C_1$–$C_4$-alkyl, $C_1$–$C_4$-alkoxy or halogen, in particular chlorine or bromine, m is 1, 2 or 3, n is 0, 1, 2, 3 or 4 and the sum of m and n is at most 5, it being possible for the radicals $R^4$ of a phenyl nucleus to be different within the definitions given.

Another preferred group of binders of type iii) are copolymers based on N-hydroxyphenylmaleimides, in particular those with structural elements of the formula II and vinyl compounds which are free from carboxyl groups.

Examples of suitable vinyl comonomers are:
a) styrene types, for example styrene, α-methylstyrene, p-methylstyrene or p-hydroxyphenylstyrene;
b) esters or amides of α,β-unsaturated acids, for example methyl acrylate, acrylamide, the corresponding methacrylic compounds or methyl maleate;
c) Nitriles of α,β-unsaturated acids, for example acrylonitrile or methacrylonitrile;
d) halogen-containing vinyl compounds, for example vinyl chloride, vinyl fluoride, vinylidene chloride or vinylidene fluoride;
e) vinyl esters, for example vinyl acetate, or
f) vinyl ethers, for example methyl vinyl ether or butyl vinyl ether.

The proportion of vinyl components is as a rule 0 to 95 mol %, preferably 0-75 mol % and particularly preferably 0-50 mol %, based on the total content of monomer units.

Homopolymers of structural units of the formula II and copolymers with vinyl compounds are known and are described, for example, in Belgian Patent Specification 613,801 and in Kobunshi Kagaku 26, 593-601 (1969) (Chem. Abstr. 72, 21964n). Turner et al. furthermore report, in Photopolymer Conference, Ellenville Oct. 1985, pages 35-47, on the use of such comonomers with vinyl compounds as binders in positive photoresists.

Another particularly preferred group of binders of type iii) are copolymers based on N-hydroxymaleimides, in particular those with structural elements of the formula II, allyl compounds and if appropriate other vinyl compounds.

These compounds are, in particular, copolymers containing 30-100 mol %, based on the total polymer, of structural units of the formula II, as defined above, and of the formula III, the proportion of radicals of the formula II, based on the total content of II and III, making up 5 to 95 mol %

$$-CH_2-CH-, \quad \text{(III)}$$
$$\quad\quad | $$
$$\quad\quad CH_2$$
$$\quad\quad | $$
$$\quad\quad A$$

in which A is selected from the group of radicals consisting of halogen, cyano or structural units of the formulae IV to IX

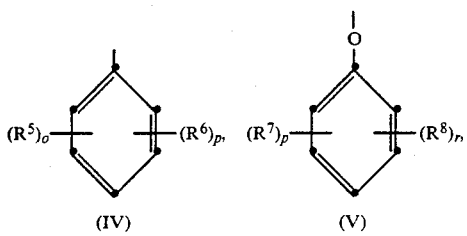

(IV)　　(V)

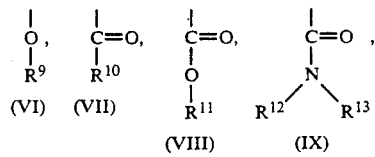

(VI)　(VII)　(VIII)　(IX)

in which $R^5$ and $R^7$ independently of one another are hydroxyl or glycidyl groups of the formula Xa or Xb

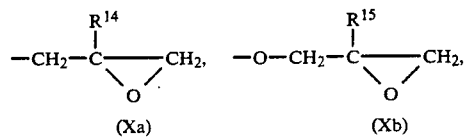

(Xa)　　(Xb)

$R^6$ and $R^8$ independently of one another are $C_1$-$C_4$-alkyl, $C_1$-$C_4$-alkoxy or halogen, o and q independently of one another are 0, 1, 2, or 3,
p and r independently of one another are 0, 1, 2, 3, 4 or 5, and the sums of o+p and q+r may be at most 5, $R^9$ is hydrogen, $C_1$-$C_{20}$-alkyl, a glycidyl radical of the formula Xa or a radical of the formula VII, $R^{10}$ is hydrogen, $C_1$-$C_{20}$-alkyl, cycloalkyl with 5 to 7 ring C atoms, phenyl, naphthyl or benzyl, $R^{11}$ is hydrogen, $C_1$-$C_{20}$-alkyl or a glycidyl radical of the formula Xa and the groups $R^{12}$ and $R^{13}$ independently of one another are hydrogen, $C_1$-$C_{20}$-alkyl, cycloalkyl with 5 to 7 ring C atoms, substituted or unsubstituted aryl or aralkyl or a glycidyl radical of the formula Xa, or, together with the common nitrogen atom, form a five- or six-membered heterocyclic ring, and $R^{14}$ and $R^{15}$ independently of one another are hydrogen or methyl, it being possible for the radicals $R^5$ to $R^{15}$ and A of a polymer molecule to be different within the definitions given.

Particularly preferred binders of type iii) are copolymers containing 50-100 mol %, based on the total polymer, of structural units of the formulae II and III.

Binders of type iii) consisting essentially of structural elements of the formulae II and III in which the amount of elements II makes up 10-80 mol %, based on the amount of II and III, are particularly preferred.

Copolymers containing structural units of the formulae II and III as defined above, in which A is selected from the group comprising radicals of the formulae IV, V, VI, VIII and IX, $R^5$ and $R^7$ are glycidyl groups of the formulae Xa or Xb, $R^9$, $R^{11}$ and at least one of the radicals $R^{12}$ or $R^{13}$ are a glycidyl group of the formula Xa and o and q independently of one another are 1, 2, or 3, are especially preferred binders of type (iii).

Binders of type iii) which contain structural units of the formulae II and III, as defined above, in which A is a group of the formula VI and $R^9$ is a group of the formula Xa, or in which A is a group of the formulae IV or V, $R^5$ and $R^7$ are glycidyl groups of the formula Xb, o and q are 1 or 2 and p and r are 0 are particularly preferred.

Other binders of type iii) are copolymers containing at least 50 mol %, based on the total polymer, of structural elements of the formulae II and III and, as the residual amount, structural elements which are derived from vinyl compounds with no carboxyl groups selected from the group consisting of styrene types, esters or amides of αβ-unsaturated acids, nitriles of αβ- unsaturated acids, halogen-containing vinyl compounds, vinyl esters and vinyl ethers.

Copolymers of N-hydroxyphenylmaleimides and allyl compounds have not previously been described.

They can be prepared by a) subjecting compounds of the formulae IIa and IIIa

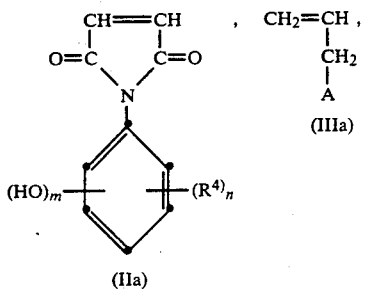

in which $R^4$, A, m and n are as defined above, to free radical polymerization, if appropriate in the presence of further monomers which can be polymerized by free radical polymerization, or b) subjecting compounds of the formulae IIb and IIIa

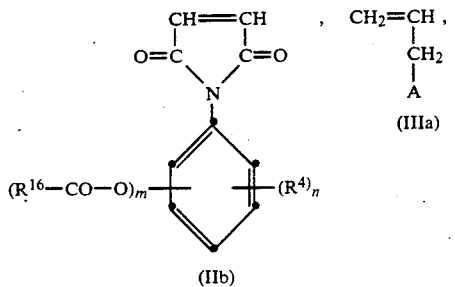

which $R^4$, A, m and n are as defined above and $R^{16}$ is a monovalent hydrocarbon radical, preferably $C_1$-$C_4$-alkyl, to free radical polymerization, if appropriate in the presence of other monomers which can be polymerized by free radical polymerization, and converting the product into a copolymer as defined above by hydrolysis of the $R^3$—CO-group.

The molecular weights of the N-(hydroxyphenyl)-maleimide/allyl copolymers are as a rule between 500 and 100,000 (weight-average).

The compounds of the formulae IIa and IIb are known per se or can be prepared by standard reactions. Further details in this context are to be found in U.S. Pat. Specification No. 4,289,699. The allyl compounds of the formula IIIa are likewise known and in some cases are commercially available.

$C_1$-$C_4$-Alkyl $R^1$, $R^2$, $R^3$, $R^4$, $R^6$ and $R^8$ are straight-chain or branched, preferably straight-chain, alkyl radicals. Examples of such groups are methyl, ethyl, n-propyl, isopropyl, n-butyl or sec.butyl. Methyl is preferred.

The alkyl part of $C_1$-$C_4$-alkoxy, $R^1$, $R^2$, $R^3$, $R^4$, $R^6$ or $R^8$ is as defined above. Methoxy is preferred.

Halogen $R^1$, $R^2$, $R^3$, $R^4$, $R^6$ or $R^8$ is fluorine, chlorine, bromine or iodine. Chlorine or bromine, in particular bromine, is preferred.

If any radicals are $C_1$-$C_{20}$-alkyl, these are preferably straight-chain groups. However, they can also be branched alkyl groups.

Examples of $C_1$-$C_{20}$-alkyl radicals are methyl, ethyl, n-propyl, isopropyl, n-butyl, sec.butyl, tert.butyl, n-pentyl, isopentyl, n-hexyl, n-heptyl, n-octyl, 2-ethylhexyl, n-nonyl, n-decyl, n-undecyl, n-dodecyl, n-tetradecyl, n-hexadecyl, n-octadecyl or n-eicosyl. $C_1$-$C_8$-alkyl radicals of this type, especially the straight-chain radicals, are preferred, and methyl or ethyl is particularly preferred.

Halogen A is fluorine, chlorine, bromine or iodine. Chlorine or bromine, in particular chlorine, is preferred.

Cycloalkyl $R^{10}$, $R^{12}$ and $R^{13}$ with 5 to 7 ring C atoms is as a rule cyclopentyl, cyclohexyl or cycloheptyl, but in particular cyclohexyl. These radicals are unsubstituted or alkyl-substituted.

Examples of substituted or unsubstituted aryl $R^{12}$ or $R^{13}$ are phenyl and naphthyl. Examples of possible substituents are alkyl groups, in particular methyl, alkoxy groups, in particular methoxy, halogen atoms, in particular chlorine or bromine, and cyano groups.

Specific examples of substituted aryl radicals are o-, m- or p-tolyl, xylyl or chlorophenyl. Phenyl is the preferred aryl radical.

Optionally substituted aralkyl $R^{12}$ or $R^{13}$ is, for example benzyl, α-methylbenzyl or α,α-dimethylbenzyl. The radicals mentioned above as examples for aryl are also possible substituents here.

Specific examples of substituted aralkyl radicals are 4-methylbenzyl or 4-methoxybenzyl. Benzyl is preferred.

The index m in the structural element of the formula II is preferably 1 or 2, particularly preferably 1. The index n in the structural element of the formula II is preferably 0, 1 or 2, particularly preferably 0.

The component b) of the negative resist according to the invention contains at least one compound with at least two epoxide groups or at least two vinyl ether groups or at least one epoxide and one vinyl ether group in the molecule.

Compounds with at least two vinyl ether groups which can be used are, for example, divinyl ethers of aliphatic, cycloaliphatic, aromatic or araliphatic diols.

Examples of preferred compounds of this type are divinyl ethers of $C_2$-$C_{12}$-aliphatic diols, polyethylene glycols, polypropylene glycols, polybutylene glycols, dimethylolcyclohexanes, mono- or dinuclear aromatic diphenols and mononuclear araliphatic diols.

Examples of specific compounds from these classes of compounds are the divinyl ethers of ethylene glycol, trimethylene-1,3-diol, tetramethylene-1,4-diol, 1-methylpropane-1,3-diol, octamethylene-1,8-diol, diethylene glycol, triethylene glycol, dipropylene glycol, tripropylene glycol, dibutylene glycol, tributylene glycol, HO—$(CH_2)_2$—O—$(CH_2)_4$—O—$(CH_2)_2$—OH, bis-1,4-methylolcyclohexane, hydroquinone, resorcinol, bisphenol A, bisphenol F and bis-methylolbenzene.

Polyvinyl ethers of novolaks can also be used. Preferred components b) are compounds with at least two epoxide groups in the molecule.

In addition, it is also possible to use relatively small amounts of monofunctional epoxy resins in combination with polyfunctional epoxy resins.

In principle, all the non-basic resins used in epoxide compound technology are suitable as component b).

Examples of epoxy resins are:

I) Polyglycidyl and poly-(β-methylglycidyl) esters obtainable by reaction of a compound with at least two carboxyl groups in the molecule and epichlorohydrin or glycerol dichlorohydrin or β-methyl-epichlorohydrin. The reaction is advantageously carried out in the presence of bases.

Aliphatic polycarboxylic acids can be used as the compound with at least two carboxyl groups in the molecule. Examples of these polycarboxylic acids are oxalic acid, succinic acid, glutaric acid, adipic acid, pimelic acid, suberic acid, azelaic acid, sebacic acid or dimerized or trimerized linoleic acid.

However, cycloaliphatic polycarboxylic acids, for example tetrahydrophthalic acid, 4-methyltetrahydrophthalic acid, hexahydrophthalic acid or 4-methylhexahydrophthalic acid can also be used.

Aromatic polycarboxylic acids, for example phthalic acid, isophthalic acid or terephthalic acid, can furthermore be used.

II) Polyglycidyl or poly-(β-methylglycidyl) ethers obtainable by reaction of a compound with at least two free alcoholic hydroxyl groups and/or phenolic hydroxyl groups and a suitably substituted epichlorohydrin under alkaline conditions, or in the presence of an acid catalyst and subsequent treatment with an alkali.

Ethers of this type are derived, for example, from acyclic alcohols, such as ethylene glycol, diethylene glycol and higher poly(oxyethylene) glycols, propane-1,2-diol or poly-(oxypropylene) glycols, propane-1,3-diol, butane-1,4-diol, poly-(oxytetramethylene) glycols, pentane-1,5-diol, hexane-2,4,6-triol, glycerol, 1,1,1-trimethylolpropane, pentaerythritol and sorbitol, and from polyepichlorohydrins.

However, these are also derived, for example, from cycloaliphatic alcohols, such as 1,3- or 1,4-dihydroxycyclohexane, bis-(4-hydroxycyclohexyl)-methane, 2,2-bis(4-hydroxycyclohexyl)-propane or 1,1-bis-(hydroxymethyl)-cyclohex-3-ene.

The epoxide compounds can also be derived from mononuclear phenols, for example from resorcinol or hydroquinone; or they are based on polynuclear phenols, for example on bis-(4-hydroxyphenyl)-methane, 4,4'-dihydroxydiphenyl, bis-(4-hydroxyphenyl) sulfone, 1,1,2,2-tetrakis(4-hydroxyphenyl-ethane, 2,2-bis-(4-hydroxyphenyl)-propane or 2,2-bis-(3,5-dibromo-4-hydroxyphenyl)-propane and on novolaks obtainable by condensation of aldehydes, for example formaldehyde, acetaldehyde, chloral or furfuraldehyde, with phenols, such as phenol, or with phenols which are substituted by chlorine atoms or $C_1$-$C_9$-alkyl groups in the nucleus, for example 4-chlorophenol, 2-methylphenol or 4-tert.butylphenol, or are obtainable by condensation with bisphenols, as described above.

III) Examples of poly-(S-glycidyl) compounds are di-S-glycidyl derivatives, which are derived from dithiols, for example ethane-1,2-dithiol or bis-(4-mercaptomethylphenyl) ether.

IV) Examples of cycloaliphatic epoxy resins are bis-(2,3-epoxycyclopentyl) ether, 2,3-epoxycyclopentyl-glycidyl ether, 1,2-bis-(2,3-epoxycyclopentyloxy)-ethane, vinylcyclohexane dioxide, limonene dioxide, dicyclopentadiene dioxide, 4-oxatetracyclo[6,2,1,0$^{2.7}$ 0$^{3.5}$]undec-9-yl glycidyl ether, 1,2-bis-(4-oxatetracyclo[6,2,1,0$^{2.7}$ 0$^{3.5}$]undec-9-yl-oxy)-ethane, the 3,4-epoxycyclohexylmethyl ester of 3', 4'-epoxycyclohexanoic acid and its 6,6'-dimethyl derivative, the bis-(3,4-epoxycyclohexanoic acid ester) of ethylene glycol or 3-(3,4-epoxycyclohexyl)-8,9-epoxy-2,4-dioxaspiro[5,5]-undecane.

However, it is also possible to use epoxy resins in which the 1,2-epoxide groups are bonded to different hetero atoms or functional groups; these compounds include, for example, the glycidyl ether-glycidyl ester of salicylic acid.

If desired, a mixture of epoxy resins can be used in the compositions according to the invention.

Particularly preferred epoxy resins are polyglycidyl ethers of novolaks which are formed by reaction of formaldehyde with a phenol, or of the abovementioned aliphatic diols, in particular butane-1,4-diol. The cycloaliphatic epoxy resins are especially preferred epoxy resins.

Polyglycidyl compounds which can be dispersed in water in the non-cured state are particularly preferred as component b). These are as a rule relatively low molecular weight epoxide compounds with other polar groups, such as hydroxyl, ether or ester groups, which must be present alongside the epoxide groups in an amount such that the dispersibility in aqueous-alkaline solutions is guaranteed. However, they can also be relatively high molecular weight compounds which contain, alongside the epoxide groups, a sufficient amount of polar groups to achieve water- o dispersibility.

Examples of preferred low molecular weight polyepoxides of this type are polyglycidyl ethers which are derived from tetramethyloltetrahydropyran-4-one or -4-ol, and polyglycidyl esters which are derived from epoxidized fatty acids and tetramethylolcyclohexanol, -cyclohexanone, -tetrahydropyran-4-ol or -tetrahydropyran-4-one. Examples of such compounds are described in Swiss Patent A-358,930 and in U.S. Pat. No. A-3,558,535.

Particularly preferred water-dispersible epoxy resins are polyglycidyl ethers of tetramethylolcyclohexanol or -cyclohexanone and di- or triglycidyl glycerol ethers. The tetramethylol-cyclohexanol or -cyclohexanone glycidyl ethers are known from European Patent A-135,477.

A large number of known cationic photoinitiators which have been tried in the art for epoxy resins can be employed as component c) of the mixtures according to the invention. These are, for example, onium salts with weakly nucleophilic anions. Examples of these are halonium salts, as mentioned under formula II in European Patent A-153,904, iodosyl salts, as mentioned under formula IV in European Patent A-153,904, sulfonium salts, as mentioned under formula III of European Patent A-153,904, sulfoxonium salts, such as are described, for example, in European Patents A-35,969, 44,274, 54,509 and 164,314, or diazonium salts, as described, for example, in U.S. Pat. No. A-3,708,296.

A review of other customary onium salt initiators is to be found in "UV-Curing, Science and Technology" (Editor: S.P. Pappas, Technology Marketing Corp., 642 Westover Road, Stanford, CT, USA).

Preferred photoinitiators are metallocene salts, such as are described, for example, in European Patent A-94,914 and especially in European Patent A-94,915.

The statements in these publications are likewise the subject of the present description.

The preferred photoinitiators include the compounds of the formulae XI, XII and XIII $$[R_h^{16}-I-R_j^{17}]^{\oplus} \quad [LQ_m]^{\ominus}, \quad \text{(XI)}$$

-continued

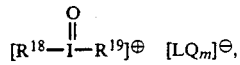

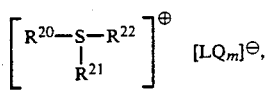

in which h is 1 and j is 1 or h is 2 and j is 0, and $R^{16}$ and $R^{17}$, where $h=1$ and $j=1$, independently of one another are monovalent carbocyclic-aromatic $C_6-C_{18}$ radicals which are unsubstituted or carry 1 to 3 substituents, and $R^{16}$, in the case where $h=2$ and $j=0$, is a divalent, carbocyclicaromatic $C_{12}-C_{18}$ radical which is unsubstituted or carries 1 to 3 substituents, $R^{18}, R^{19}, R^{20}, R^{21}$ and $R^{22}$ independently of one another assume one of the meanings of $R^{17}$, L is selected from the group consisting of B, P, As and Sb, Q is a halogen atom or some of the radicals Q in one anion $LQ_m$- can also be hydroxyl groups, and m is an integer which corresponds to the valency of L reduced by one.

Examples of monovalent carbocyclic-aromatic $C_6-C_{18}$ radicals are phenyl, naphthyl, anthryl and phenanthryl. Phenyl is preferred. Substituents which may be present in these radicals are alkyl, preferably $C_1-C_6$-alkyl, such as methyl, ethyl, n-propyl, isopropyl, n-butyl, n-pentyl or n-hexyl, alkoxy, preferably $C_1-C_6$-alkoxy, such as methoxy, ethoxy, n-propoxy, n-butoxy, n-pentoxy or n-hexoxy, halogen, such as fluorine, chlorine, bromine or iodine, amino groups, cyano groups or nitro groups.

An example of divalent carbocyclic-aromatic $C_{12}-C_{18}$ radicals is biphenyl-2,2'-diyl.

Examples of preferred halogen atoms Q are chlorine or, in particular, fluorine. Preferred anions $LQ_m^-$ are $BF_4^-$, $PF_6^-$, $AsF_6^-$, $SbF_6^-$ and $SbF_5(OH)^-$.

The especially preferred metallocene initiators in the context of this invention include the compounds of the formula XIV

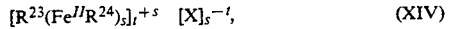

in which s is 1 or 2, t is 1, 2, 3, 4 or 5, X is a non-nucleophilic anion, $R^{23}$ is a π-arene and $R^{24}$ is an anion of a π-arene, preferably cyclopentadienyl.

Examples of π-arenes $R^{23}$ and anions of π-arenes $R^{24}$ are to be found in European Patent A-94,915.

Examples of preferred π-arenes $R^{23}$ are toluene, xylene, ethylbenzene, cumene, methoxybenzene, methylnaphthalene, methoxynaphthalene, pyrene, perylene, stilbene, diphenylene oxide and diphenylene sulfide.

Cumene, methylnaphthalene or stilbene are particularly preferred.

Examples of non-nucleophilic anions $X^-$ are $FSO_3-$, anions $[LQ_m]$, as defined above.

Preferred anions are derived from partly fluorinated or perfluorinated aliphatic or partly fluorinated or perfluorinated aromatic carboxylic acids or, in particular, from partly fluorinated or perfluorinated aliphatic or partly fluorinated or perfluorinated aromatic organic sulfonic acids, or are preferably anions $[LQ_m]-$.

Examples of anions X are $BF_4^-$, $PF_6^-$, $AsF_6^-$, $SbF_6^-$, $SbF_5OH^-$, $CF_3SO_3^-$, $C_2F_5-SO_3^-$, n-$C_3F_7SO_3^-$, n-$C_4F_9SO_3^-$, n-$C_6F_{13}SO_3^-$, n-$C_8F_{17}SO_3-$, $C_6F_5SO_3-$, phosphotungstate ($PO_{40}W_{12}3-$) or silicotungstate ($SiO_{40}W_{12}4-$).

$PF_6^-$, $AsF_6^-$, $SbF_6^-$, $CF_3SO_3^-$, $C_2F_5SO_3^-$, n-$C_3F_7SO_3^-$, n-$C_4F_9SO_3^-$, n-$C_6F_{13}SO_3^-$, n-$C_8F_{17}SO_3-$, are preferred.

It is also possible to use combinations of these metallocene salts with oxidizing agents. Such combinations are described in European Patent A-126,712.

To increase the light efficiency, sensitizers are preferably added, depending on the type of initiator.

Examples of these are polycyclic aromatic hydrocarbons or aromatic keto compounds. Specific examples of preferred sensitizers are mentioned in European Patent A-153,904.

The mixture according to the invention can also contain other additives d) customary in the art of negative resists. Examples of such additives are wetting agents, flow control agents, stabilizers, dyes, pigments, fillers, adhesion promoters, plasticizers and additional resins. Additional resins are in general used to modify the mechanical properties of the coating. Examples of these are styrene or acrylate-based vinyl copolymers, polyesters, polyamides or silicone resins. These additional resins are as a rule added in small amounts, preferably of up to 10% by weight, based on the total mixture. They must be compatible with the other constituents of the mixture and should be soluble in organic solvents.

Catalysts, accelerators and curing agents for the epoxide component can furthermore be added to the mixtures. These additives have the effect of post-curing the epoxide component during any after-treatment with heat; if appropriate, this post-curing step is carried out after development of the photoresist.

The compositions according to the invention preferably contain 10–90% by weight of binder a), 5–80% by weight of epoxy resin or vinyl ether b), 0.5–20% by weight of photoinitiator c) and 0–15% by weight of the additive d). The proportions of the individual components here in each case make up 100% and the amounts stated are based on the total amount.

The compositions especially preferably contain, based on the total amount, 30–85% by weight of binder a), 10–60% by weight of epoxide compound or vinyl ether b), 1–10% by weight of photoinitiator c) and 0–10% by weight of additives d).

To produce coatings, components a)–c) and if appropriate d) are dissolved in a suitable solvent. The choice of solvent and the concentration depend chiefly on the nature of the compositions and on the coating process. The solvent should be inert, that is to say it should not undergo a chemical reaction with the components, and it should be possible to remove the solvent again during drying after the coating operation.

Known coating processes are, for example: whirler-coating, dipping, knife coating, curtain coating processes, brushing on, spraying or reverse roll coating.

The composition according to the invention can furthermore be transferred as a dry film from a temporary flexible carrier onto a substrate. Such a process is described, for example, in European Patent A-153,904.

The amount applied (coating thickness) and nature of the substrate (coating carrier) depend on the desired field of application. It is particularly advantageous that the compositions according to the invention can be used in widely varying coating thicknesses. This coating thickness range comprises values from about 0.5 μm to more than 100 μm.

Possible fields of use of the compositions according to the invention are the use as photoresists for electronics (as an electroplating resist, etch resist or solder resist), the production of printing plates, such as offset printing plates or screen printing plates, use for chemical milling or use as a microresist in the production of integrated circuits.

The possible coating carriers and the processing conditions for the coated substrates vary accordingly.

Films of polyester or cellulose acetate or paper coated with plastic, for example, are used for photographic recording of information; specially treated aluminium is used for offset printing plates and copper-lined laminates are used for the production of printed circuits. The coating thicknesses for photographic materials and offset printing plates are preferably about 0.5 to 10 μm; and for printed circuits they are 1 to about 100 μm.

After the coating operation, the solvent is as a rule removed by drying and a coating of the photoresist on the carrier results.

The photosensitivity of the compositions according to the invention as a rule ranges from the UV region (about 200 nm) up to about 600 nm and thus spans a very wide range. A large number of the most diverse types of light sources are therefore used. Both point sources and sources which emit over an area (lamp carpets) are suitable. Examples are: carbon arc lamps, xenon arc lamps, mercury vapour lamps, if appropriate doped with metal halides (metal-halogen lamps), fluorescent lamps, argon glow lamps, electron flash lamps and photographic floodlights.

The distance between the lamp and the image material according to the invention can vary, for example between 2 cm and 150 cm, depending on the intended use and lamp type or intensity. Laser light sources, for example argon ion lasers or krypton ion lasers with intense emission lines (Ar lasers) at 457, 476, 488, 514 and 528 nm, are particularly suitable. With this type of exposure, a photo mask in contact with the photopolymer coating is no longer necessary; the controlled laser beam writes directly onto the coating. The high sensitivity of the materials according to the invention is very advantageous here and allows high writing speeds at relatively low intensities. This method can be used to produce printed circuits in the electronics industry, lithographic offset printing plates or relief printing plates and photographic image recording materials.

After image-wise exposure of the material and before development, it may be advantageous to carry out a heat treatment for a relatively short time. Only the portions already exposed are post-cured by heat. This heat treatment is particularly advisable for metallocene photoinitiators. It can take place in conventional ovens, for example in convection ovens, or with IR radiation, for example by irradiation with IR lasers, or in microwave equipment. The temperatures applied are in general 50°-150° C., preferably 80°-130° C.; the curing time is as a rule between 1 and 15 minutes.

After the exposure and any after-treatment with heat, the non-exposed areas of the photoresist are removed with a developer in a manner which is known per se.

Particularly preferred developers are aqueous-alkaline solutions such as are also used for development of naphthodiazide-quinone coatings. These include, in particular, solutions of alkali metal silicates, phosphates, hydroxides and carbonates. If appropriate, relatively small amounts of wetting agents and/or organic solvents can also be added to these solutions.

Development with organic solvents is also possible. Examples of suitable solvents are cyclohexanone, 2-ethoxyethanol, acetone, MEK and mixtures of these solvents.

After the exposure and development, the relief image can be subjected to another heat treatment (second stage post-curing by heat). The remaining epoxide groups or vinyl ether groups thereby react with the phenolic hydroxyl groups of the binder or polymerize with each other. For this, the catalysts and accelerators customary in epoxy resin or vinyl ether chemistry can already be added during the coating operation (component d), but they should not interfere with the exposure.

This additional matrix formation by heat gives particularly resistant and durable relief images which, like coatings of cured epoxy resins, are distinguished by good thermomechanical, chemical and electrical properties, in particular stability, adhesion and a high volume resistivity.

The invention therefore also relates to a process for the production of relief structures comprising the following operating steps:
  a) coating of a substrate with a radiation-sensitive composition as defined above,
  b) exposure of the coated substrate with a given pattern of actinic radiation, if appropriate
  c) after-treatment with heat,
  d) a development stage and
  e) if appropriate after-treatment of the developed system with heat.

The expression "exposure with a given pattern of actinic radiation" comprises both exposure through a photo mask containing a given pattern, for example a positive slide, and exposure by a laser beam which, for example, is moved by computer control over the surface of the coated substrate and in this way produces an image.

The invention furthermore relates to a process for the production of protective coatings comprising the following operating steps:
  a) coating of a substrate with a radiation-sensitive composition as defined above,
  b) exposure of the radiation-sensitive coating over its entire surface and
  c) if appropriate after-treatment of the exposed system with heat.

The invention moreover relates to the use of the compositions defined above for the production of protective coatings and relief structures.

The following examples illustrate the invention in more detail.

Preparation Examples

Example 1

Copolymer of p-maleimidylphenol and butyl vinyl ether:

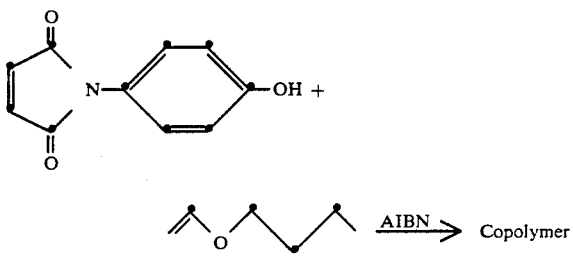

The following components are introduced into a 2.5 liter sulfating flask equipped with a stirrer, thermometer, reflux condenser and nitrogen inlet and outlet:

| | | |
|---|---|---|
| 378.3 g | (2.0 mol) | of p-maleimidylphenol |
| 220.3 g | (2.2 mol) | of butyl vinyl ether |
| 10.3 g | (62.7 mmol) | of α,α'-azo-bisisobutyronitrile |
| 1000.0 g | | of methyl ethyl ketone |

After rendering the system inert with nitrogen, the suspension is heated by an oil bath, while stirring. At an internal temperature of about 66°, the polymerization starts with considerable generation of heat. The oil bath is removed and the mixture is cooled with an ice bath until the vigorous reflux of the MEK subsides. The mixture is then heated by the oil bath at a temperature of 75° for 7 hours. GPC then shows virtually complete conversion of the monomer.

For analytical purposes, a sample of the polymer solution is precipitated in water and the solid polymer is filtered off and dried in vacuo (0.01 mbar) at 130° C. for several hours.

$\overline{M}_w$ = 80430 GPC, polystyrene standards
$\overline{M}_n$ = 32336 GPC, polystyrene standards
Hydroxyl group content = 4.10 equivalents/kg (titrimetrically).

USE EXAMPLES

Example I 2 coating formulations are prepared as follows:

| Resin ® M = poly-p-vinylphenol | Ia | Ib |
|---|---|---|
| Resin ® M (Maruzen Oil, Japan) ($M_w$ about 6,000) | 12.00 g | — |
| Resin ® M (Maruzen Oil, Japan) ($M_w$ about 20,000) | — | 12.00 g |
| 3,4-Epoxycyclohexylmethyl 3,4-epoxy-cyclohexanecarboxylate | 8.00 g | 8.00 g |
| Photoinitiator{[C$_5$H$_5$]Fe$^{II}$-[stilbene]}$^+$PF$_6^-$, 10% solution in cyclohexanone | 10.00 g | 10.00 g |
| Orasolrot B (Ciba-Geigy) dye | 0.04 g | 0.04 g |
| Methyl ethyl ketone/methylcellosolve 1:1 | 20.00 g | 20.00 g |

A cleaned, copper-lined printed circuit board is coated under yellow light with the solutions in a wet film thickness of 100 μm by means of a doctor blade. The film is dried at 80° C. for 30 minutes. The thickness of the photosensitive coating is about 40 μm. It is exposed through a Stouffer Sensitivity guide (optical density increments = 0.15) in addition to a Stouffer resolution guide. The light source is a 5,000 watt metal-halogen lamp (Sylvania M 061) at a distance of 65 cm from the vacuum frame. The exposure time is 15 seconds. The board is then heated at 100° C. for 10 minutes, cooled to room temperature and developed in developer Ⓐ at 20° for 90 seconds.

Result

The step wedge copied has 12–13 half-tone steps (form Ia) or 13–14 half-tone steps (form Ib). The resist image can be used, for example, as an electroplating resist for the semi-additive technique.

Developer Ⓐ

75.0 g of sodium metasilicate pentahydrate
0.4 g of Supronic ® B50 (ABM Chemicals Ltd., Stockport Cheshire GB); wetting agent 925.0 g of deionized water

Example II

Coating Solution

| | |
|---|---|
| Polymer from Example 1; 41% solution in MEK (binder polymer) | 58.50 g |
| 3,4-Epoxycyclohexylmethyl 3,4-epoxycyclohexane-carboxylate | 16.00 g |
| Photoinitiator {[C$_5$H$_5$]Fe$^{II}$-[stilbene]}$^+$PF$_6^-$, 10% solution in cyclohexane | 20.00 g |
| Orasolrot B (Ciba-Geigy) dye | 0.08 g |
| Methyl ethyl ketone/methylcellosolve 1:1 | 5.50 g |

Copper-lined laminates are coated with this solution as described in Example I and the film is dried to give a coating about 40 μm thick. After exposure according to Example I, the board is heated at 120° C. for 10 minutes, cooled and developed with dilute developer Ⓐ (A:H$_2$O = 1:1).

Result

Exposure time: 15 seconds
Heat treatment: 10 minutes/120°
Development time: Developer Ⓐ : H$_2$O = 1:1 v/v 20° C.
60 seconds
Step wedge copied: last step imaged = No. 14

The resist image developed can be used as an etch mask for etching away the copper in customary baths (for example FeCl$_3$ solution).

Example III

The production of a negative offset plate which can be developed under aqueous-alkaline conditions is described here.

Coating Solution

The coating solution of Example II (40% in MEK/MCS 1:1) is diluted to 10% solids content with MEK/MCS 1:1. The solution is applied to an electrolytically roughened anodized aluminium sheet (offset plate substrate) by means of whirler-coating (30 seconds at 500 revolutions/minute) and is dried at 80° for 15 minutes. A coating weight of 1.3 g/m$^2$ results. The coating is exposed through a Stouffer test wedge as described in Example I. The light source in this case is a 2,000 Watt metal-halogen lamp at a distance of 75 cm from the vacuum frame. After the exposure, treatment with heat and development are carried out. The developed image is inked with oily black printing ink as is customary in lithography.

Result

Exposure time: 10 seconds
Heat treatment: 10 minutes/120° C.
Development time: Developer A : H$_2$O = 1:1 v/v 20° C.
45 seconds
Step wedge copied: Last step imaged = No. 13

This printing plate allows a high print run as a result of the good mechanical (wear) properties of the crosslinked image portions.

Example IV

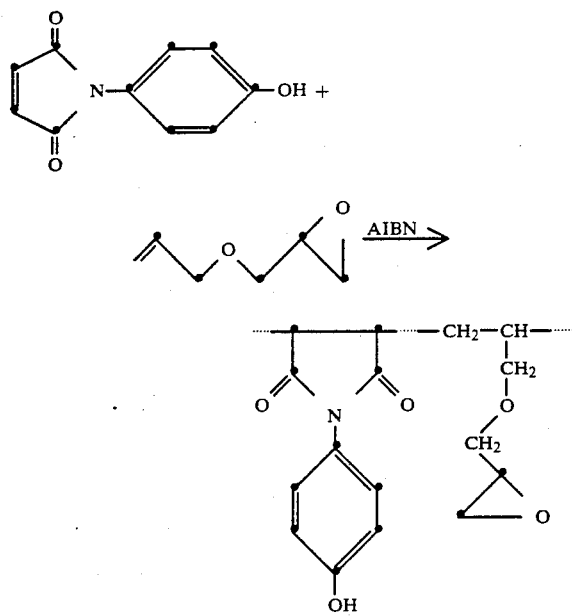

A 2.5 litre, sulfating flask equipped with a stirrer, thermometer, reflux condenser and nitrogen inlet and outlet is charged with the following components:

50.0 g (0.264 mol) of p-maleimidylphenol
270.6 g (2.37 mol) of allyl glycidyl ether
0.9 g of α,α'-azobisisobutyronitrile (AIBN).

After the system has been rendered inert with nitrogen, the suspension is heated with an oil bath, while stirring. At an internal temperature of about 70° C., the polymerization starts, with considerable generation of heat. The oil bath is removed and the mixture is cooled with an ice bath for about 10 minutes. It is then heated by the oil bath at a temperature of about 70° C. for 7 hours. The yellowish suspension is introduced into 4,000 ml of toluene, with thorough stirring, and the precipitate is filtered off and dried in vacuo at 60° C. for 14 hours. The solid product is dissolved in acetone and precipitated again from toluene. After drying in vacuo, the colourless solid copolymer is isolated.

Elemental analysis

% found: C 62.07 H 6.60 N 3.92

$\overline{M}_w = 4,600$ Gel permeation chromatography (polystyrene $\overline{M}_n = 2,529$ standards)

Composition of the random copolymer: p-Maleimidylphenol/allyl glycidyl ether = 40.6/59.4 mol % (from elemental analysis)

Epoxide group content, = 3.7 equivalents/kg (titrimetrically)

Coating Solution

| | |
|---|---|
| Poly(p-maleimidylphenol/allyl glycidyl ether) | 1.80 g |
| 3,4-Epoxycyclohexylmethyl 3,4-epoxycyclohexane-carboxylate | 1.20 g |
| Photoinitiator {[C$_5$H$_5$]Fe$^{II}$-[stilbene]}$^+$PF$_6^-$, 10% solution in cyclohexanone | 1.50 g |
| Orasolrot B (Ciba-Geigy) dye | 0.006 g |
| Methyl ethyl ketone/methylcellosolve 1:1 | 5.50 g |

A copper-lined laminate is coated with the solution analogously to Example I. Dry coating weight = about 25 g/m$^2$. After exposure according to Example I, the laminate is heated at 120° C. for 10 minutes and developed with developer Ⓐ.

Result

Exposure time: 15 seconds
Heat treatment: 10 minutes/120°
Development time: Developer Ⓐ 20° C. 30 seconds
Wedge copy: Last step imaged = No. 9

Example V

Coating Solution

| | |
|---|---|
| Resin ® M (Maruzen Oil, Japan) ($\overline{M}_w$ about 6,000) | 2.50 g |
| Bisphenol A diglycidyl ether | 3.00 g |
| ($\eta^6$-Cumene)($\eta^5$-cyclopentadienyl)iron(II) hexafluoroantimonate | 0.16 g |
| Isopropylthioxanthone | 0.08 g |
| Crystal violet | 0.004 g |
| Cyclohexanone | 8.00 g |

Processing is carried out analogously to that described under Example I:
Exposure time: 45 seconds;
Curing : 20 minutes at 110° C.
Result: The step wedge copied has 8-9 half-tone steps.

Example VI

Coating Solution

| | |
|---|---|
| Resin ® (Maruzen Oil, Japan) ($\overline{M}_w$ about 6,000) | 2.50 g |
| Bisphenol A diglycidyl ether | 3.00 g |
| Triphenylsulfonium hexafluorophosphate | 0.16 g |
| Isopropylthioxanthone | 0.08 g |
| Crystal violet | 0.004 g |
| Cyclohexanone | 8.00 g |

Processing is carried out by a procedure analogous to that described under Example I:
Exposure time: 45 seconds
Curing : 20 minutes at 110° C.
Result: The step wedge copied has 2-3, half-tone steps.

Example VII

Coating Solution

| | |
|---|---|
| Resin ® (Maruzen Oil, Japan) ($\overline{M}_w$ about 6,000) | 2.50 g |
| Bisphenol A diglycidyl ether | 3.00 g |
| Diphenyliodonium hexafluoroarsenate | 0.16 g |
| Isopropylthioxanthone | 0.08 g |
| Crystal violet | 0.004 g |
| Cyclohexanone | 8.00 g |

Processing is carried out by a procedure analogous to that described under Example I:
Exposure time: 45 seconds
Curing : 20 minutes at 60° C.
Result: The step wedge copied has 10-11 half-tone steps.

Example VIII

Coating Solution

| | |
|---|---|
| Technical grade cresol novolak (Alnovol PN 430, Hoechst) | 2.50 g |
| Bisphenol A diglycidyl ether | 3.00 g |
| ($\eta^6$-Cumene)($\eta^5$-cyclopentadienyl)iron(II) hexafluoroantimonate | 0.16 g |
| Isopropylthioxanthone | 0.08 g |
| Crystal violet | 0.004 g |
| Cyclohexanone | 8.00 g |

Processing is carried out by a procedure analogous to that described under Example I:
Exposure time: 45 seconds
Curing : 20 minutes at 100° C. –Result: The step wedge copied has 6–7 half-tone steps.

Example IX

Coating Solution

| | |
|---|---|
| Resin ® M (Maruzen Oil, Japan) ($\overline{M}_w$ about 6,000) | 2.50 g |
| Bisphenol A di(2-vinyloxy-ethyl) ether | 3.00 g |
| ($\eta^6$-Cumene)($\eta^5$-cyclopentadienyl)iron(II) hexafluoroantimonate | 0.016 g |
| Isopropylthioxanthone | 0.08 g |
| Crystal violet | 0.004 g |
| Cyclohexanone | 8.00 g |

Processing is carried out by a procedure analogous to that described under Example I:
Exposure time: 45 seconds;
Curing : 20 minutes at 50° C.
Result: The, step wedge copied has 10 half-tone steps.

Example X

Coating Solution

| | |
|---|---|
| Resin ® M* (Maruzen Oil, Japan) | 2.50 g |
| 2,2,6,6-Tetra-(2,3-epoxy-1-propoxy-methyl)-cyclohexan-1-ol | 2.50 g |
| ($\eta^6$-Cumene)($\eta^5$-cyclopentadienyl)iron(II) hexafluoroantimonate | 0.16 g |
| Isopropylthioxanthone | 0.08 g |
| Crystal violet | 0.004 g |
| Cyclohexanone | 8.00 g |

*Poly-p-vinylphenol; $\overline{M}_w$ about 6,000

The coating solution is applied to a printed circuit board with a 100μ wire doctor. The initially wet film is dried at 80° C. for 30 minutes. Exposure is carried out with the exposure apparatus described in Example I. The board is exposed for 45 seconds through a mask which covers the lands. The exposed board is precured at 110° C. for 10 minutes and then developed in developer Ⓐ for 90 seconds and post-cured at 135° C. for 1 hour. The board coated with flux (solution of 26 g of pure rosin in 100 ml of isopropanol) is placed with the coating underneath on a hot solder bath (consisting of 50% of lead and 50% of tin) at 270° C.. After 10 seconds, the board is removed from the solder bath, cooled, freed from the flux by washing with isopropanol and dried with compressed air.

Result: The coating shows no visible change such as cracks, bubbles, pores, or adhering residues of tin/lead at all.

Example XI

Example X is repeated with the modification that the epoxide 2,2,6,6-tetra-(2,3-epoxy-1-propoxy-methyl)-cyclohexan-1-ol is replaced by the same amount of glycerol polyglycidyl ether (Grilonit G 1705, EMS-CHEMIE AG). Result: No visible change in the coating after the solder bath (10 seconds/270° C.)

Example XII

Coating Solution

| | |
|---|---|
| Resin ® M (Maruzen Oil, Japan: $\overline{M}_w$~6,000) | 125 g |
| Glycerol polyglycidyl ether (Grilonit G1705, EMS-CHEMIE AG) | 125 g |
| ($\eta^6$-Cumene)($\eta^5$-cyclopentadienyl)iron(II) hexafluoroantimonate | 8 g |
| Isopropylthioxanthone | 4 g |
| Crystal violet | 0.2 g |
| 1-Methoxy-2-propanol | 150 g |
| 3-Ethylethoxypropionate | 150 g |

The coating solution is applied to a copper-lined epoxide board with an electrostatic spray coating unit with a high-speed rotating bell (T = 25,000 rpm) under a field strength of 0.3 kV/mm.

After drying at 80° C., a uniform coating 50 μm thick is obtained.

Exposure through a mask with a printed circuit image (45 seconds), curing (20 minutes at 110° C.) and development are carried out according to Example I.

The board is treated in an electroplating copper bath in accordance with the following working plan:
cleaning by dipping for 1 minute in a solution of BUZ-R at 25° C. (Dr. Ing. Max Schlötter GmbH and Co. AG),
rinsing with running water for 1 minute,
gentle etching in a solution of 120 g of ENPLATE AD485 (IMASA AG, Dällikon, Switzerland) and 20 ml of concentrated sulfuric acid per litre of water,
acid copper bath AC from Erne AG, Dällikon, 75 minutes at about 25° C. and a current density of 3 A/dm$^2$,
rinsing with tap water.

After the board has been subjected to electroplating treatment, the resist shows no damage such as bubbles, cracks and the like and can be removed cleanly by stripping with 1N sodium hydroxide solution/isopropanol 10:1. The copper coating obtained is about 50 μm thick.

What is claimed is:
1. A composition consisting essentially of
a) at least one solid film forming polyphenol which has such a content of phenolic hydroxyl groups to render the composition soluble or swellable in an aqueous-alkaline developer solution, wherein the polyphenol is selected from the group consisting of
i) a novolak which is derived from a binuclear or mononuclear substituted or unsubstituted phenol and a $C_1$–$C_6$alkehyde;
ii) a copolymer of a vinyl compound with no carboxyl groups and an alkenylphenol which contains the structural element of formula I

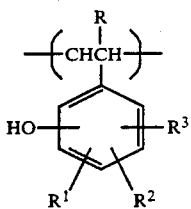
(I)

in which R is hydrogen or methyl and $R^1$, $R^2$ and $R^3$ independently of one another are hydrogen, $C_1$–$C_4$-alkyl, $C_1$–$C_4$-alkoxy, halogen or methylol; and iii) a copolymer of a vinyl compound with no carboxyl groups and a N-hydroxyphenylmaleimide which contains the structural element of formula II

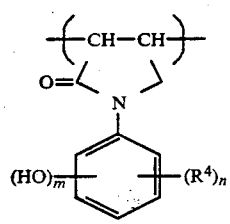
(II)

wherein $R^4$ independently is $C_1$–$C_4$-alkyl, $C_1$–$C_4$-alkoxy, halogen, m is 1,2 or 3, n is 0,1,2,3 or 4 and the sum of m and n is at most 5;

b) at least one compound, different from a), which contains at least two epoxide groups or at least two vinyl groups or at least one epoxide and one vinyl ether group in the molecule, and c) at least one cationic photoinitiator for component b) selected from the group consisting of onium salts with weakly nucleophilic anions and metallocene salts.

2. A composition according to claim 1, in which component b) is at least one compound which contains at least two epoxide groups in the molecule.

3. A composition according to claim 1, in which component b) is derived from
a polyglycidyl ether of a novolak formed by reaction of formaldehyde with a phenol,
diglycidyl ethers of aliphatic diols and
cycloaliphatic epoxy resins.

4. A composition according to claim 1, in which component b) is a polyglycidyl compound which can be dispersed in water in the non-cured state.

5. A composition according to claim 4, in which component b) is a polyglycidyl ethel of tetramethylolcyclohexanol or -cyclohexanone or a di- or triglycidyl glycerol ether.

6. A composition according to claim 1, in which the photoinitiator c) is selected from the compounds of the formulae XI, XII and XIII

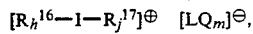
(XI)

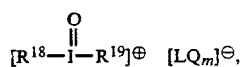
(XII)

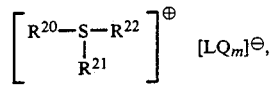
(XIII)

in which h is 1 and j is 1 or h is 2 and j is 0, and $R^{16}$ and $R^{17}$, where $h=1$ and $j=1$, independently of one another are monovalent carbocyclic-aromatic $C_6$–$C_{18}$ radicals which are unsubstituted or carry 1 to 3 substituents, and $R^{16}$, in the case where $h=2$ and $j=0$, is a divalent, carbocyclic-aromatic $C_{12}$–$C_{18}$ radical which is unsubstituted or carries 1 to 3 substituents, $R^{18}$, $R^{19}$, $R_{20}$, $R_{21}$ and $R_{22}$ independently of one another assume one of the meanings of $R^{17}$, L is selected from the group consisting of B, P, As and Sb, Q is a halogen atom, or some of the radicals Q in one anion $LQ_M^-$ can also be hydroxyl groups, and m is an integer which corresponds to the valency of L reduced by one.

7. A composition according to claim 1, in which the photoinitiator c) is a compound of the formula XIV

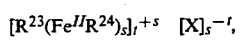
(XIV)

in which s is 1 or 2, t is 1, 2, 3, 4 or 5, X is a non-nucleophilic anion, $R^{23}$ is a π-arene and $R^{24}$ is an anion of a π-arene.

8. A composition consisting essentially of
a) at least one solid film forming polyphenol which has such a content of phenolic hydroxyl groups to render the composition soluble or swellable in an aqueous-alkaline developer solution, wherein the polyphenol is selected from the group consisting of
i) a novolak which is derived from a binuclear or mononuclear substituted or unsubstituted phenol and a $C_1$–$C_6$aldehyde;
ii) a homo- or copolymer of an alkenylphenl which contains the structural element of formula I

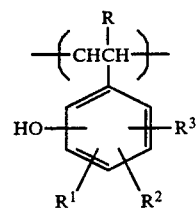
(I)

in which R is hydrogen or methyl and $R^1$, $R^2$ and $R^3$ independently of one another are hydrogen, $C_1$–$C_4$-alkyl, $C_1$–$C_4$-alkoxy, halogen or methylol; and ii) a homo- or copolymer of N-hydroxyphenylmaleimide which contains the structural element of formula II

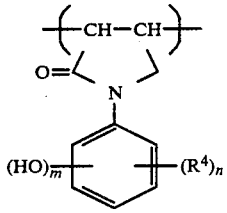
(II)

wherein $R^4$ independently is $C_1$-$C_4$-alkyl, $C_1$-$C_4$-alkoxy or halogen, m is 1 2 or 3, n is 0,1,2,3 or 4 and the sum of m and n is at most 5;

b) at least one compound, different from a), which contains at least two epoxide groups or at least two vinyl groups or at least one epoxide and one vinyl ether group in the molecule, and c) a least one cationic photoinitiator for component b) selected from the group consisting of onium salts with weakly nucleophilic anions and metallocene salts; wherein said composition contains 30-100 mol %, based on total polymer, of structural units of the formula II and formula III, the proportion of radicals of the formula II, based on the total amount of II and III, making up 5 to 95 mol %

$$-CH_2-CH-, \qquad (III)$$
$$\qquad | $$
$$\qquad CH_2$$
$$\qquad | $$
$$\qquad A$$

in which A is selected from the group of radicals consisting of halogen, cyano and structural units of the formulae IV to IX

(IV)

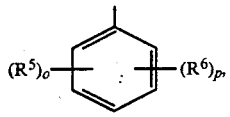
(V)

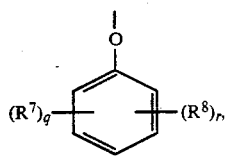
(VI)

(VII)

(VIII)

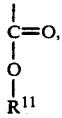

-continued

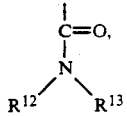
(IX)

in which $R^5$ and $R^7$ independently of one another are hydroxyl or glycidyl groups of the formula Xa or Xb

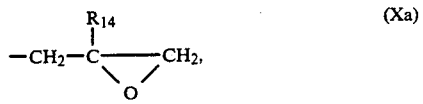
(Xa)

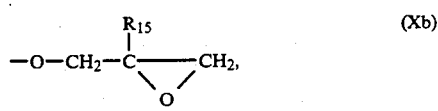
(Xb)

$R^6$ and $R^8$ independently of one another are $C_1$-$C_4$-alkyl, $C_1$-$C_4$-alkoxy or halogen, o and q independently of one another are 0,1,2 or 3, p and r independently of one another are 0,1,2,3,4 or 5, and the sums, o=p and q=r are at most 5, $R^9$ is hydrogen, $C_1$-$C_{20}$-alkyl, a glycidyl radical of the formula Xa or a radical of the formula VII, $R^{10}$ is hydrogen, $C_1$-$C_{20}$-alkyl, cycloalky with 5 to 7 ring C atoms, phenyl, naphthyl or benzyl, $R^{11}$ is hydrogen, $C_1$-$C_{20}$-alkyl or a glycidyl radical of the formula Xa and the groups $R^{12}$ and $R^{13}$ independently of one another are hydrogen, $C_1$-$C_{20}$-alkyl, cycloalkyl with 5 to 7 ring C atoms, substituted or unsubstituted aryl or aralkyl or a clycidyl radical of the formula Xa, or, together with the common nitrogen atom, form a five- or six-membered heterocyclic ring, and $R^{14}$ and $R^{15}$ independently of one another are hydrogen or methyl.

9. A composition according to claim 8, containing copolymers with 50-100 mol %, based on the total polymer, of structural units of the formulae II and III.

10. A composition according to claim 8, in which the binder essentially consists of structural elements of the formulae II and III, the proportion of elements II making up 10-80 mol %, based on the amount of II and III.

11. A composition according to claim 8, in which A is selected from the group consisting of radicals of the formulae IV, V, VI, VIII and IX, $R^5$ and $R^7$ are glycidyl groups of the formulae Xa or Xb, $R^9$, $R^{11}$ and at least one of the radicals $R^{12}$ or $R^{13}$ are a glycidyl group of the formula Xa and o and q independently of one another are 1, 2, or 3.

12. A composition according to claim 8, in which A is a group of the formula VI and $R^9$ is a group of the formula Xa, or in which A is a group of the formulae IV or V, $R^5$ and $R^7$ are glycidyl groups of the formula Xb, o and q are 1 or 2 and p and r are 0.

13. A composition according to claim 8, containing copolymers with at least 50 mol %, based on the total polymer, of structural elements of the formulae II and III and, as the residual amount, structural elements which are derived from vinyl compounds with no carboxyl groups selected from the group consisting of styrene, esters or amides of α,β-unsaturated acids, nitriles of α,β-unsaturated acids, halogen-containing vinyl compounds, vinyl esters and vinyl ethers.

* * * * *